United States Patent [19]

Nagel

[11] 4,255,593
[45] Mar. 10, 1981

[54] SALTS OF POLYCHLORINATED PHENOLS

[75] Inventor: Fritz J. Nagel, Memphis, Tenn.

[73] Assignee: Chapman Chemical Company, Memphis, Tenn.

[21] Appl. No.: 123,380

[22] Filed: Feb. 21, 1980

[51] Int. Cl.³ .................. C07C 39/32; C07C 39/34; C07C 39/36
[52] U.S. Cl. .................................................. 568/776
[58] Field of Search ........................................ 568/776

[56] References Cited

U.S. PATENT DOCUMENTS

| | | | |
|---|---|---|---|
| 1,991,329 | 2/1935 | Mills | 568/776 |
| 2,131,259 | 9/1938 | Stoesser | 568/776 |
| 2,188,944 | 2/1940 | Fox et al. | 568/776 |
| 2,818,425 | 12/1957 | Heywood | 568/776 |
| 2,833,830 | 5/1958 | Rigterink | 568/776 |
| 3,320,325 | 5/1967 | Widiger et al. | 568/776 |
| 3,333,020 | 7/1967 | Howald | 568/776 |

FOREIGN PATENT DOCUMENTS 722210 11/1965 Canada .................................... 568/776
916770 7/1954 Fed. Rep. of Germany .

*Primary Examiner*—Joseph E. Evans
*Attorney, Agent, or Firm*—Fred Philpitt

[57] ABSTRACT

In the process for the manufacture of salts of halogenated phenols the economy is improved and health and pollution hazards are reduced by mixing an alkaline agent and the halogenated phenol with a small amount of a liquid medium that is solvent for the alkaline agent, conducting a reaction between the components in a closed system until a dry or almost dry product is obtained, agitating the mixture during at least a part of the liquid medium removal step and discharging the product in particulate form from the closed system.

17 Claims, No Drawings

SALTS OF POLYCHLORINATED PHENOLS

BACKGROUND OF THE INVENTION

Halogenated phenols are widely used fungicidal agents. These water-insoluble halogenated phenols can be converted into water-soluble compounds by reaction with an alkaline agent. Although simple in theory, this reaction is connected with numerous problems. For instance, since both the insoluble compounds and the soluble compounds are toxic, strict measures must be taken to avoid environment contamination and worker exposure. Also, drying the soluble product involves complicated safety risks because dusting problems arise and because an additional granulation step often is required to give the dried product a form appropriate for use. Further, the drying step must not involve too high temperatures since this might degrade the product and/or generate still more toxic by-products. This limitation complicates and extends the drying step and reduces cost efficiency.

When the costs of drying and the dangers of handling dusts become too severe, an alternative solution is to package and ship the product without removing the liquid. This is not often an economical solution since containers for liquids usually are more expensive than those for solids and the added weight and volume increases shipping costs.

The above mentioned problems have become so troublesome in recent years that one of the largest manufacturers of sodium pentachlorophenate monohydrate ceased manufacturing operations because of the excessive expense of upgrading both procedures and equipment in order to meet current standards for worker's safety and pollution abatement. This manufacturer's process involved the following reaction:

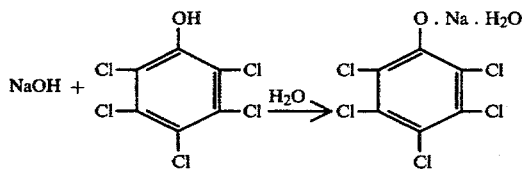

This reaction was carried out in enough water to dissolve the NaOH and to hold the sodium chlorophenate product in solution. Since the solubility of the sodium pentachlorophenate is somewhat limited in water, the weight of the water that had to be removed at the end of the reaction was in the range of from 3 to 5 times the weight of the solid product. The apparatus conventionally used to remove this water was a fluidized bed dryer, which consumed substantial amounts of energy. A drum drier could have been used instead of a fluidized bed drier but the product of a drum drier are flakes that are subject to considerable dusting. A fluidized bed dryer is objectionable because the higher process temperatures required for efficient operation favor the formation of dioxins, which are notorious for extreme toxicity.

OBJECTS OF THE INVENTION

Accordingly, it is an object of this invention to provide a method for safe and economic production of salts of halogenated phenols.

Another object of this invention is to reduce environmental contamination and worker exposure to dusts occasioned by drying the products from the reaction carried out in a liquid medium.

Another object of this invention is to reduce the energy requirements for removing liquid from the reaction medium and from the product.

Another object of this invention is to conduct the drying operations under conditions in which a nondusting particulate product of selected size and shape is recovered.

Another object of this invention is to provide methods and means whereby the temperature at which the drying operations are conducted can be minimized to avoid the occurrence of side reactions or degradation of the product.

Another object of this invention is to provide a process for conducting the reaction in a liquid medium within a substantially closed system in which a solid product is recovered in any of several desired forms with a minimum expenditure of energy and with essentially zero worker exposure to or environmental contamination by the reactants, the product, or the liquid medium.

THE PRESENT INVENTION

Briefly, these and other objects of this invention are achieved by a method for reacting halogenated phenols with alkaline material to form an alkali salt of the halogenated phenol, which method comprises the steps of mixing the alkaline material and the halogenated phenol with a liquid that is a solvent for the alkaline material, conducting the reaction in a closed system, removing the liquid from the mixture in the system until a dry or almost dry product is obtained, agitating the mixture during at least a part of the liquid removal step and discharging the product in particulate form from the closed system.

Considered from another aspect, the present invention relates to a method for reacting at least one halogenated phenol with an alkaline material capable of forming an alkali metal salt of the halogenated phenol comprising the steps of mixing the alkaline material and at least one halogenated phenol with a liquid that is a solvent for the alkaline material, conducting the reaction in a closed reaction zone, removing liquid from the mixture in the system until a dry or almost dry product is obtained, agitating the mixture during at least a part of the liquid removal step and discharging the product in particulate form from the closed system.

Of the common halogenated phenols, the chlorinated phenols are preferred. The aromatic ring may contain one to five chlorine atoms and mixtures thereof. The tri-, tetra- and pentachlorophenols are, however, preferred.

Any alkaline material capable of forming an alkali salt with the chlorinated phenol may be used in the reaction. The alkali metal hydroxides are preferred and especially sodium hydroxide.

Since the reactants are preferably in the form of solids (e.g. the sodium hydroxide and the pentachlorophenol) and since temperatures high enough to melt the reactants cannot be used (due to degradation and byproduct formation problems) a liquid medium is added in order to increase the reaction speed. The liquid should be a solvent for at least one of the reactants, preferably the alkaline material, and it is preferred that it is also a solvent, at least in part, for the alkali salt of the halogenated phenol. Water and alcohols, especially polyols, are preferred liquids. Mixtures of different liquids may be used and in that case azeotropic mixtures are preferred in order to simplify evaporation. The amount of liquid shall be kept as low as possible. An amount much less than that required to retain all of the reaction product in solution is preferred. This is advantageous not only in reducing the amount of liquid that must be handled and removed to dry the product, but also in reducing the power requirements for the mixing equipment since the torque needed to mix a slurry or pasty mass is greater than that required to mix wet solids in which the free volume between the solids is not filled with liquid. Suitable liquid amounts have been found to be 2%–50% by weight of the halogenated phenol, and preferably between 5 and 10 percent.

All of the reactants can be mixed to start the reaction or small amounts, especially of the liquid, may be added continuously to the reactor containing the balance of the reactants. A thorough mixing for efficient reaction can be obtained by agitation in the reactor. The agitation is preferably conducted during both charging reaction and liquid removal.

An elevated temperature of 140°–212° F. may be used during the reaction and for this purpose heat may be added. It is preferred to conduct the reaction at reflux boiling conditions, whereby the desired temperature may be controlled by pressure adjustment, especially application of vacuum.

The reaction time can be varied between several minutes and several hours depending upon the temperature, pressure, type of agitator used, agitator speed and force, reflux conditions, etc. The optimum reaction time for any set of variables can be readily determined by one skilled in the art by rather routine experimentation.

After the aforesaid liquid medium has served its purpose of expediting reaction between the alkaline medium and the halogenated phenol, it may be desirable to remove part or all of the liquid medium. Such liquid removal may be desirable to simplify subsequent handling and use of the reaction product, or to minimize health hazards during the manufacturing process. The manner of drying can be very important to economy, health safety and product quality. A special advantage of the present process is that any removal of the liquid medium is performed in the same vessel that the reaction takes place so that extra material transfer steps are avoided. The removal of liquid medium can be started after the reaction step is completed or during the reaction. Several methods of liquid removal can be used, for example by the addition of a liquid absorbing medium or more preferably the evaporation. In a sense the liquid removal steps can be a simple continuation of the reaction step, especially if the reaction is conducted under reflux conditions whereby the same means for heat addition, means for possible pressure regulation, means for liquid vapor withdrawal and means for vapor condensation can be used, but instead of returning the condensed liquid to the reactor, as in the reaction step, the liquid medium is removed in the drying step and preferably stored in a part of a closed system. The use of vacuum during removal of the liquid is preferred. The removal of liquid medium shall normally be continued until a solid and not moist product is obtained. However, discharging a slightly wet product may be suitable for special granulation processes (such as extrusion and chopping to form pieces of the product).

In order to obtain the desired economy and safety in the present manufacturing method, it is not sufficient to merely be able to react and remove liquid medium in the above described simple manner, but is also necessary to obtain the product in a free-flowing particulate or granular form which is non-dusting, easily handled and easily dissolved. Such a product can be obtained by the present invention since it has been found that the alkali halophenols in the present manufacturing method can be autogranulated in a simple manner. Furthermore, it has been found possible to control the particle density, particle size, particle shape and particle distribution of the product by varying such things as the agitator speed, the speed of water removal, the method of water removal, the degree of reduced pressure that is used for liquid removal the temperature in the reactor, whether or not additives (such as borax and sodium sulfate) are added to the reactor, etc. Depending on the variables, these properties can be obtained simply by agitation during the drying step, i.e. with the same reactor and equipment and without special granulation steps.

It has also been found that the size and shape of the product can be controlled to range from a rather fine dustless powder to comparatively large granules or prills by adjusting the amount of liquid used; the type of liquid, the time, rate, pressure and temperature of the liquid removal cycle; the shear forces imposed on the product during liquid removal, additives designed to promote reaction rate and additives designed for other purposes including specific requirements of formulated products.

From the above description it can be understood that one of the main advantages of the present invention is that all the steps required to arrive at a suitable solid product from the raw materials namely the reaction, the drying, and the particulation steps, can be performed in the same vessel. This is not only an advantage from an economic or efficiency point of view but above all it has the advantage that the entire process can be conducted in a closed system with a minimum of material transport and hence a maximum of safety.

The closed system of the present invention shall at least include a vessel with means for raw material charging and product discharging as well as agitation means. Preferably an internal mixer is used (preferably the double planetary type) which does not have too high an agitation speed but which traverses as much as possible of the reactor volume. Preferably the system of the invention includes heating means for increasing the reaction mixture temperature, for refluxing and for liquid removal. Preferably the system also includes condensing means for refluxing the liquid during reaction and for removing the liquid during drying. Preferably the system also includes pressure regulating means, normally pressure reduction means, which permits boiling at suitably low temperatures and at an increased rate. Preferably the closed system also includes a vessel for storing the withdrawn and condensed liquid for reuse in the system with subsequent reactant batches.

Hence, a preferred system for practice of this invention includes a closed reaction vessel fitted with an internal double planetary mixer, a vacuum system for operating the vessel under reduced pressure; a reflux/takeoff condenser and a reaction medium storage vessel. The vacuum system provides a means for removal of the excess liquid from the product at relatively low temperatures so that power requirements and product degradation are minimized. Vacuum distillation of the liquid also provides an extremely effective way to reduce the temperature within the reaction vessel and reduce cycle times.

Another type of reaction vessel which could be used is a ribbon blender which can be sealed and equipped with a take-off condenser or a compounding extruder, preferably of the twin screw type. In this later example a reaction zone can be established in one portion of the barrel followed by a vented zone that communicates with the vacuum condenser system. Following the venting zone a comparatively dry product is then extruded as rods or ribbons which are chopped or diced into pellets or granules.

In any case, whatever type of sealed reaction vessel is selected for use in combination with a take-off condenser, the amount of liquid may be minimized and the reaction contained within a sealed vessel so that no contamination to the atmosphere, as by dusting, will occur and the liquid medium, when volatilized, can easily be recovered and recycled to the system without the danger of contamination or, in the case of organic solvents, without the danger of fire or explosion.

EXAMPLES

The invention can better be understood in connection with the following specific examples which place primary emphasis upon a process for converting water-insoluble pentachlorophenol to water-soluble sodium pentachlorophenate by reaction with an alkaline material such as sodium hydroxide. However, it is to be understood that it is not intended that the invention be limited by these specific examples. Unless otherwise indicated in the examples that follow, the equipment used in the system included an externally jacketed reaction vessel which could be heated or cooled by a heat transfer medium. The vessel had a lid which could be sealed, a charge port and a double planetary internal mixer; and a reflux/take-off condenser and a vacuum system connected to the vessels. The parts are by weight unless otherwise indicated.

EXAMPLE 1

350 lbs of pentachlorophenol (PCP) prills sold under the trade name of Dowicide EC-7 (88% pentachlorophenol and 12% tetrachlorophenol) and 55 lbs of sodium hydroxide prills are charged into a reaction vessel having a reflux condenser. The vessel is then closed, the agitators in the vessel are started and 50 psi steam is circulated in the jacket. 45 lbs. of water are then introduced into the vessel through a charge port over a 2 to 4 minute period. An exothermic reaction begins immediately, bringing the reactants to reflux temperature (210° F.) within 3-5 minutes after the water addition is complete. With the condenser set in the reflux position, the reaction is continued for 30 minutes. The condenser is then set for water take-off and the reaction vessel evacuated, reaching an internal vacuum of 28-29 inches of mercury within 3-10 minutes. Nearly the full amount of water originally added is removed in 15-30 minutes. Since the boiling point of water during the application of vacuum quickly goes below the batch temperature, the water is removed very rapidly, and at the end of the water removal cycle, the batch temperature is reduced sufficiently to permit immediate removal of the product without further cooling.

The product was in the form of non-dusting beads approximately 1/16 to 3/16 inches in diameter. Since process temperatures never exceeded 210° F., the amount of dioxin did not exceed that which was in the PCP feedstock.

EXAMPLE II

The procedure of Example I was repeated except that the liquid medium used was 45 lbs of an azeotropic mixture (b.p. 206° F.) comprised of 53% by weight of the methylether of propylene glycol (Dowanol PM) and 47% by weight of water. Similar results were obtained as in Example I and it was observed that the reaction mixture contained so little liquid that if a sample was removed from the reaction vessel at the end of the reflux period and cooled to room temperature, the product was found to be hard and friable.

EXAMPLE III

The reactor was charged as in Example I with 400 lbs. PCP, 62 lbs. of sodium hydroxide and only 10 lbs. of water. At the end of 30 minutes refluxing at 210° F. it was found that the conversion to sodium pentachlorophenate was 99+%.

This example indicates the astonishingly small quantity of reaction medium required in the practice of this invention. The amount of water added at the start is much less than required to dissolve the sodium hydroxide (an estimated 20 lbs. of water is needed to dissolve all the sodium hydroxide at 210° F.). And, competing with the sodium hydroxide for the available water is the final product, sodium pentachlorophenate, an estimated 5% of which dissolves in the water reaction medium at 210° F.

The overall significance of this is important in terms of reducing the energy needed in a chemical reaction where there is a liquid reaction medium which subsequently must be removed. By way of comparison in the prior art commercial process for making sodium pentachlorophenate 1,400 to 1,800 lbs. of water was considered necessary in order to satisfactorily react 400 lbs. of PCP with 62 lbs. of sodium hydroxide. The energy costs for removing this conventionally employed quantity of water represents, at current costs, about 21% of the total cost of the sodium pentachlorophenate as opposed to only 2% in the practice of the instant invention.

EXAMPLE IV

The reaction vessel of Example I was charged with 60.18 lbs. PCP, 9.5 lbs. sodium hydroxide and 30.32 lbs. of methanol. Upon addition of the sodium hydroxide, an exothermic reaction was initiated, limited in temperature to the boiling point of the methanol (148° F.). The PCP, soluble in the methanol, quickly reacted with the sodium hydroxide to form the sodium salt which, because of its lower solubility in methanol and continuing methanol removal, rapidly formed a slurry which became progressively more viscous, changing to a friable particulate solid which at the time the process was terminated had altered to a free-flowing powder. The vacuum at the time of termination was about 27 inches of mercury. Final product temperature was approximately 190° F. The sodium pentachlorophenate recovered was a 98+% yield and was in the form of a non-dusting, free-flowing powder averaging less than 200 mesh particle size. The entire process took place with zero worker or environmental exposure and with essentially zero danger from the highly volatile and flammable methanol which was collected for reuse.

The product, in addition to high purity, assayed less than 4 ppm hexa and octachlorodibenzo-p-dioxin content. Operating the process under vacuum conditions reduced the opportunity for the formation of other impurities by oxidation. The apparent specific gravity of the powder was 32 lbs./cubic foot.

EXAMPLE V

The procedure of Example IV was repeated except that for five hours the processing under vacuum took place without addition of heat to the mixing vessel jacket. Then two hours after applying 210° F. temperature, the process was terminated. Instead of a fine powder as in the previous Example, the product consisted of hard, irregularly shaped spheres in the 3/16" to ⅜" diameter size range.

For many uses, this physical shape is very desirable since it resists dusting in subsequent handling and because it dissolves more slowly in water when used. In cases where very rapid solution in water is desired for use, a small amount of starch or other water-swelling agent can be incorporated in the reaction mass, to cause rapid breakup of the spheres, when subjected to water, thereby reducing the time to obtain complete solution.

EXAMPLE VI

The procedure of Example IV was repeated except that at the termination of the drying process, 4% propylene glycol was added to the fine powder mix and stirring continued for 15 minutes. Soft prills were formed and the bulk density increased from 32 to 56 lbs./cu.ft.

EXAMPLE VII

The reaction vessel was charged with the following materials in parts by weight:

| Tetrachlorophenol | 23.60 |
|---|---|
| Sodium hydroxide | 6.00 |
| Sodium metaborate | 6.00 |
| Methanol | 20.00 |
| Phenyl mercuric lactate | 0.40 |

After mixing for 10 minutes, a vacuum is drawn and mixing continued for 60 minutes. Then heat, 125° F., is added to the bowl jacket and agitation continued for 80 minutes. The process is terminated and the process, less the methanol (recovered for reuse), is a mixture of sodium tetrachlorophenate, excess sodium hydroxide and sodium metaborate. This product has been sold in liquid form for many years for sapstain control in green lumber, at a 25% active ingredient content. Preparation of the product in dry form has considerable economic and fuel saving advantages since it would require one-fourth the number of containers, and one-fourth the transportation cost and the elimination of expensive solvents required to maintain freeze-thaw stability in the shipping container.

Heretofore, however, manufacture of this product in solid, particulate form was completely impractical on an economic basis simply because the low sales volume of the product could not justify the elaborate and costly equipment needed to dry the product after mixing in a liquid medium without loss of PMA and without exposure to workers and the environment.

EXAMPLE VIII

The following ingredients were utilized:

| PCP (96% assay) | 180 lbs. |
|---|---|
| NaOH | 29 lbs. |
| Water | 24 lbs. |
| Sodium tetraborate pentahydrate | 66 lbs. |
| Sodium tetraborate decahydrate (borax) | 213 lbs. |
| Water | 11 lbs. |

The PCP, NaOH and 24 lbs. water were added to the reactor of Ex. 1, stirred and refluxed at 210° F. for 30 minutes at atmospheric pressure. Then the penta hydrate was added, followed at once with the decahydrate and agitation was continued for 15 minutes. The other 11 lbs of water was added and agitation continued for 10 minutes more. The product was in the form of free-flowing, non-dusting particulate particles.

This example illustrates the manufacture of a widely used wood antifungal composition comprised of sodium pentachlorophenate and borax using the process of this invention. Ordinarily these two materials are dry blended together in powdered form, which creates an irritating dust problem that is difficult and expensive to control. By using the process of this invention the sodium pentachlorophenate is prepared as in the foregoing examples except that the water is not removed by vacuum distillation. Rather a mixture of sodium tetraborate decahydrate and sufficient sodium tetraborate pentahydrate are added to the sodium pentachlorohydrate slurry to absorb the excess or water of hydration.

EXAMPLE IX

The procedure of Example I was followed except that the reflux time was 5 min. instead of 30, water take-off is at atmospheric pressure (no vacuum) and water take-off time is 50-70 minutes instead of 15-30.

In a number of experiments that were performed, it was found that the apparent specific gravity and particle size of the sodium pentachlorophenate could be adjusted by making simple changes in the processing conditions for instance to yield a powder of 32 lbs./cu.ft., ⅜" diameter spheres of 45 lbs./cu.ft., or 1/16" prills of 64 lbs./cu.ft.

It has also been discovered that in the practice of this invention, the starting PCP feedstock need not be in particulate form but that the water-insoluble PCP can be used in the form of large chunks or blocks by adding sufficient alkali to fully form the soluble alkaline salt of PCP.

The block of PCP actually is dissolved by progressive formation of the sodium salt which is water-soluble. One would think that the rate of NaPCP formation from block PCP and subsequent solution would be too slow for practical commercial use. Surprisingly, however, rapid solution occurs. For example, a quantitative yield of sodium pentachlorophenate can be obtained in less than one hour by reacting a 500 gram block of PCP with a 3% stoichiometric excess of sodium hydroxide at 190° F.

While the double planetary mixer was employed in the foregoing Examples, other types of processing equipment could be used such as single planetary mixers, sigma arm mixers or Banbury mixers.

The key to an integral part of the invention seems to be how the liquid mass being stirred thickens and how the agitator breaks up the mass. For instance, in Example IV, the immediate application of heat (and vacuum) rapidly converts the initial slurry to soft, small, friable, agglomerated lumps which, as drying proceeds, are broken down by the agitator into a fine powder.

On the other hand, in Example V, omission of heat for several hours (but with vacuum) allowed the mass being mixed to lose liquid much more slowly and this caused much larger and stronger lumps to form. Then, on application of heat, the lumps "skinned over", forming a dried, hard outside shell wherein integrity of the lumps or pellets was maintained during the balance of the drying. On the other hand, with a different liquid medium (water instead of methanol), the "right" conditions can be set up for prills with hard skins.

It is also possible to produce relatively large cross-sectional pieces of sodium pentachlorophenate, which are sometimes preferred. Conventional technology requires that the particulate NaPCP be put through a briquetting process to obtain the desired larger size pieces. And for certain uses, the NaPCP is formulated with other materials, the combination of which is then made into pellets or briquettes of the desired size.

The process of this invention allows a one-step production of a hard, strong piece of NaPCP in almost any desired form—slab, rod or square (that is, a rectangular, square or round cross-section via extrusion, cut to any desired length). To do this a heavy duty sigma arm mixer, equipped with a bottom-end extruder for emptying the charge is needed. The exterior of the mixing chamber is equipped with a steam heating jacket allowing jacket temperatures up to about 230° F. The dry PCP (400 lbs) and sodium hydroxide (63 lbs.) is charged to the mixer, the mixer closed and 35 lbs. of water introduced into the mixer, which is vented through a reflux condenser.

The batch is mixed for one hour at 200° F. and then removed from the mixer via extrusion, the extrudate at 200° F. having a stiff, plastic consistency. Upon cooling, the extrudate will be hard and strong and contain 7% free water. The cross-sectional shape of the extrudate is determined by the shape of the exit die on the extruder; the continuous extrudate is then cut to desired length. Also, as mentioned above, a similar process can be conducted in a compounding extruder.

While the foregoing examples have been directed to the use of NaOH in the formation of alkali metal salts of halogenated phenols, potassium hydroxide could be used just as well and no invention could be involved in using in place of NaOH such alkaline materials as alkalol amines, primary amines, etc.

Also, whereas specific times and temperatures have been set forth, the only real criteria is any combination of time and temperature that will result in completion of the reaction. Generally the temperature can range between 140° F. and 212° F. depending on pressure, time, degree of agitation, etc.

When the sodium salt of pentachlorophenol is mentioned in the foregoing examples and in the following claims, it will be understood that the product is actually the monohydrate.

I claim:
1. A method for reacting at least one halogenated phenol with an alkali to form a product of an alkali metal salt of the halogenated phenol comprising the steps of
    (a) mixing an alkali and at least one halogenated phenol at a temperature below the melting points of the reactants with a liquid medium that is a solvent for the alkali, said liquid medium being used in an amount which is less than that required to fill the free volume of the solids obtained by reacting said alkali and said halogenated phenol,
    (b) conducting the reaction in a closed reaction zone,
    (c) removing liquid from the mixture in the system until a dry or almost dry product is obtained,
    (d) agitating the mixture during at least a part of the liquid removal step, and
    (e) discharging the dry or almost dry product from the closed system.
2. The method of claim 1 in which said at least one halogenated phenol comprises a chlorinated phenol.
3. The method of claim 1 in which sait at least one halogenated phenol comprises pentachlorophenol.
4. The method of claim 1 in which said alkali comprises sodium hydroxide.
5. The method of claim 1 in which said liquid comprises water.
6. The method of claim 1 in which said liquid comprises an alcohol.
7. The method of any one of claims 1, 5, or 6 in which said liquid comprises an azeotropic mixture.
8. The method of claim 1 in which said halogenated phenol and the alkali are fed to a closed reaction zone and mixed therein with said liquid by agitation.
9. The method of claim 1 in which the amount of liquid mixed with the alkali and the halogenated phenol is between 2 and 50 percent by weight of the amount of the halogenated phenol.
10. The method of claim 8 in which the amount of liquid is between 2 and 50 percent by weight of the amount of the halogenated phenol.
11. The method of claim 8 in which the amount of liquid is between 1 and 50 percent by weight of the amount of the halogenated phenol.
12. The method of claim 1 in which the amount of liquid is between 5 and 30 percent by weight of the halogenated phenol.
13. The method of claim 1 in which the reaction is conducted at an elevated temperature.
14. The method of claim 12 in which the liquid is refluxed during the reaction.
15. The method of claim 1 in which liquid is removed by vacuum distillation.
16. The method of claim 1 in which the collected liquid is stored in a part of the closed system.
17. The method of claim 1 in which said dry or almost dry product is in the particulate form.

* * * * *